US012050208B2

United States Patent
Kita et al.

(10) Patent No.: US 12,050,208 B2
(45) Date of Patent: Jul. 30, 2024

(54) ODOR EVALUATION DEVICE, ODOR EVALUATION METHOD AND DEVICE FOR PREPARING GAS FOR ODOR EVALUATION

(71) Applicants: Shimadzu Corporation, Kyoto (JP); National University Corporation, Iwate University, Morioka (JP)

(72) Inventors: Junichi Kita, Kyoto (JP); Masao Miyazaki, Morioka (JP); Motoo Kinoshita, Kyoto (JP)

(73) Assignees: SHIMADZU CORPORATION, Kyoto (JP); NATIONAL UNIVERSITY CORPORATION, IWATE UNIVERSITY, Morioka (JP)

( * ) Notice: Subject to any disclaimer, the term of this patent is extended or adjusted under 35 U.S.C. 154(b) by 215 days.

(21) Appl. No.: 17/510,745

(22) Filed: Oct. 26, 2021

(65) Prior Publication Data
US 2022/0137006 A1    May 5, 2022

(30) Foreign Application Priority Data
Nov. 2, 2020 (JP) ................. 2020-183426

(51) Int. Cl.
*G01N 33/00* (2006.01)
*G01N 30/06* (2006.01)
(Continued)

(52) U.S. Cl.
CPC ......... *G01N 30/06* (2013.01); *G01N 33/0001* (2013.01); *G01N 33/0018* (2013.01);
(Continued)

(58) Field of Classification Search
CPC .............................. G01N 33/0001
See application file for complete search history.

(56) References Cited

U.S. PATENT DOCUMENTS 3,882,713 A * 5/1975 Nishida ............. G01N 33/0001
　　　　　　　　　　　　　　　　　　　　　73/23.34
6,015,536 A * 1/2000 Lokkesmoe ........... B01D 53/38
　　　　　　　　　　　　　　　　　　　　　423/210

FOREIGN PATENT DOCUMENTS

JP　　　　2014048224 A　　3/2014
JP　　　　2018-036147 A　　3/2018
(Continued)

OTHER PUBLICATIONS

Arnaud Hallier et al., "New gas chromatography-olfactometric investigative method, and its application to cooked *Silurus glanis* (European catfish) odor characterization", Journal of Chromatography A, 1056 (2004), pp. 201-208.
(Continued)

*Primary Examiner* — Jamel E Williams
*Assistant Examiner* — Alex T Devito
(74) *Attorney, Agent, or Firm* — Maier & Maier, PLLC

(57) ABSTRACT

An odor evaluation device, including: a gas chromatograph including a separation column configured to temporally separate a plurality of components contained in an odoriferous analysis-target gas; a timing detector configured to detect, for each of the plurality of components, a timing at which the component exits from the separation column; a gas collector configured to collect, into a sample bag, a gas containing all or some of the components exiting from the separation column when the analysis-target gas is passed through the separation column; a timing setter configured to allow a setting of a timing at which a component contained in the gas to be collected into the sample bag exits from the separation column; and a gas introducer configured to introduce a dilution gas into a passage connecting the separation column and the sample bag.

15 Claims, 4 Drawing Sheets

(51) Int. Cl.
*G01N 30/02* (2006.01)
*G01N 30/88* (2006.01)

(52) U.S. Cl.
CPC . *G01N 2030/025* (2013.01); *G01N 2030/062* (2013.01); *G01N 2030/8868* (2013.01)

(56) References Cited

FOREIGN PATENT DOCUMENTS

| | | |
|---|---|---|
| JP | 3218125 U | 9/2018 |
| JP | 3219160 U | 12/2018 |
| JP | 2020073930 A | 5/2020 |

OTHER PUBLICATIONS

Office Action issued on Oct. 24, 2023, in corresponding Japanese Application No. 2020-183426, 4 pages.
Office Action issued on Aug. 30, 2023, in corresponding Chinese Application No. 202111201437.8, 29 pages.
Office Action issued on May 9, 2024, in corresponding Chinese Application No. 202111201437.8, 24 pages.

* cited by examiner

Fig. 4

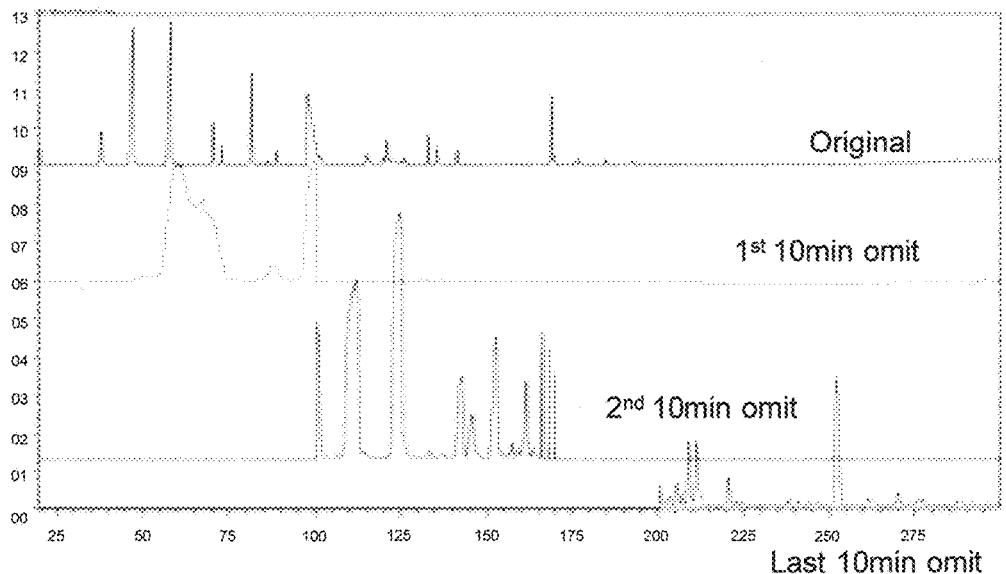

Fig. 5

| Start | Stop | Intensity | Odor characteristics | Degree of contribution | | Start | Stop | Intensity | Odor characteristics | Degree of contribution |
|---|---|---|---|---|---|---|---|---|---|---|
| 15.0 | 15.7 | medium | pickles, Sulfur-containing | △ | ↔ | 15.0 | 15.7 | strong | pickles | ○ |
| 15.7 | 16.3 | strong | Acetic acid | ○ | | 15.7 | 16.3 | strong | Acetic acid, Burned | ○ |
| 16.3 | 18.0 | strong | grain, Burned sweet, potato | ○ | ⇠⇢ | 16.3 | 18.0 | strong | Burned sweet | ○ |
| 18.0 | 18.7 | weak | odorless | × | ⇔ | 18.0 | 18.7 | weak | odorless | × |
| 18.7 | 19.5 | weak | odorless | × | ⇔ | 18.7 | 19.5 | weak | odorless | × |
| 19.5 | 20.3 | strong | Sorry, smelly, odor of food | ○ | ⇠⇢ | 19.5 | 20.3 | strong | smelly, flower | ○ |
| 20.3 | 21.5 | medium | tatami, dry fruits | △ | | 20.3 | 21.5 | strong | tatami | ○ |
| 21.5 | 22.5 | medium | flower | △ | | 21.5 | 22.5 | weak | smelly | × |
| 22.5 | 23.5 | weak | vinyl, sweet | × | | 22.5 | 23.5 | weak | vinyl, sweet | × |
| 23.5 | 25.0 | medium | heavy flower | △ | | 23.5 | 25.0 | strong | heavy flower | ○ |

Fig. 6

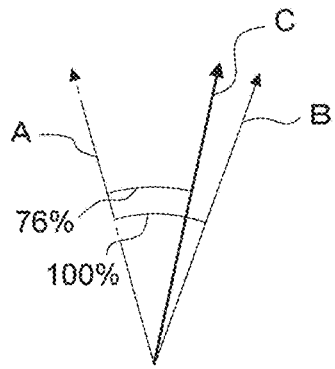

ODOR EVALUATION DEVICE, ODOR EVALUATION METHOD AND DEVICE FOR PREPARING GAS FOR ODOR EVALUATION

TECHNICAL FIELD

The present invention relates to an odor evaluation device and method, as well as a device for preparing a gas for odor evaluation.

BACKGROUND ART

Some of the fragrances added to beverages, foodstuffs, cosmetics, detergents and other products are made to imitate aromas emitted from natural products, such as flowers, herbaceous plants or fruits (natural fragrance). Many of the natural fragrances are complex odors containing various components mixed together. They produce a wide variety of odors depending on the kinds of components and the content ratio of each component. Furthermore, mixing a plurality of constituents can produce an odor that is unpredictable from the original odor of each individual constituent. Not all components forming a natural fragrance contribute to the formation of its odor; some components whose ratios of contribution are extremely low or even zero are also contained. On the site of the development of fragrances, there has been the desire to know which one or more of the components contained a natural fragrance are minimally needed to reproduce the odor of the fragrance concerned.

An omission test is commonly used as a method for determining whether or not a specific component contained in a natural fragrance is a contributor to the odor formation. An odor obtained by combining a plurality of components (complex odor) may be an odor that is unimaginable from the original odor of each individual constituent. Therefore, testing each individual component of the complex odor is not useful for creating the odor of the complex odor. An omission test is a method in which an omission odor is prepared by removing a component or components of the odor from a target odor (complex odor), and the omission odor is compared with the target odor to evaluate, based on the similarity between the two odors, whether or not the component or components removed from the target odor are contributors to the odor formation.

In the omission test, a sniffing gas chromatograph-mass spectrometer (GCMS) or similar device is normally used to detect as many odoriferous components as possible in the target odor as well as perform quantitative and qualitative analyses of those components. Mixing the detected components should ideally result in the original odor. However, in most cases, it is impossible to detect all components contained in the target odor. Therefore, in practice, the mixture will not have the original odor. To deal with this problem, a perfumer guesses a component which is short of and adjusts its concentration to reproduce the original odor. However, in the case of a complex odor, a component or components that do not contribute to the entire odor are present among the components of the odor. Accordingly, after a group of components and their respective concentrations for reproducing the target odor has been determined, one or more components are removed from that group to determine the minimal set of components required for composing the original odor. Thus, the typical omission test requires a significant amount of expert knowledge and techniques as well as a considerable length of time.

To address this problem, for example, an odor evaluation device as described in Patent Literature 1 can be used, with which a test similar to the typical omission test can be performed automatically and efficiently within a short period of time. The odor evaluation device described in Patent Literature 1 includes a gas chromatograph, odor gas collection unit, sniffing port, and odor sensor. The gas chromatograph has a separation column configured to separate a target odor gas. The odor gas collection unit is configured to individually collect, into a plurality of sample bags, an "all-component odor gas" (i.e., an odor gas which contains all components that exit from the separation column when the target odor gas is passed through the separation column) and a plurality of "omission odor gases" (i.e., odor gases each of which is obtained by removing a specified component or components from the group of components that exit from the separation column while the target odor gas is repeatedly passed through the separation column) The sniffing port allows the user to sniff each of the odor gases collected in the sample bags and perform sensory evaluation. The odor sensor is configured to detect the odor of each of the odor gases. Based on the result of the sensory evaluation or that of the detection by the odor sensor, the device calculates an index value which represents the similarity between the all-component odor gas and each of the omission odor gases.

The first bag is used to collect all components of the target odor gas without omission, to confirm that the original odor is correctly reproduced from those components, i.e., that none of the components has changed its odor due to thermal denaturing caused by the heat from the column (or other elements).

Subsequently, the chromatographic region corresponding to the components to be omitted is changed for each sample bag so as to identify a component or components which are minimally required to reproduce the original odor.

The odor gas collection unit in the previously described odor evaluation device has a plurality of attachment ports to which sample bags can be removably attached, and a switching valve which guides the components from the separation column to one of the attachment ports. With this configuration, the plurality of odor gases (all-component odor gas and a plurality of gases each of which has one or more components omitted) can be individually collected in a plurality of separate sample bags, and the odor gases collected in the sample bags can be sequentially subjected to a measurement.

CITATION LIST

Patent Literature

Patent Literature 1: JP 2018-036147 A

SUMMARY OF INVENTION

Technical Problem

Some of the components exiting from the separation column are highly adsorptive and may partially adhere to a passage. In particular, those components are likely to adsorb to a soft material used in the sealing area of the switching valve. Therefore, as the number of attachment ports is increased and more switching valves are required, the easy-to-adsorb material will also be used in larger amounts, allowing the adsorption of a component to occur more easily. The adsorption of a component to a passage or switching valve (or other elements) may possibly lead to the loss of that component from the odor gas to be collected into a sample bag. In that case, the odor gas collected in the sample bag will not be the originally intended one.

The problem to be solved by the present invention is to obtain a gas for odor evaluation with which the odor of an analysis-target gas can be correctly evaluated.

Solution to Problem

The first aspect of the present invention is an odor evaluation device including:
a gas chromatograph including a separation column configured to temporally separate a plurality of components contained in an odoriferous analysis-target gas;
a timing detector configured to detect, for each of the plurality of components, the timing at which the component exits from the separation column;
a gas collector configured to collect, into a sample bag, a gas containing all or some of the components exiting from the separation column when the analysis-target gas is passed through the separation column;
a timing setter configured to allow the setting of the timing at which a component contained in the gas to be collected into the sample bag exits from the separation column; and
a gas introducer configured to introduce a dilution gas into a passage connecting the separation column and the sample bag.

The second aspect of the present invention is an odor evaluation method including the steps of passing an odoriferous analysis-target gas through a separation column of a gas chromatograph, collecting, into a sample bag, a gas containing all or some of the components exiting from the separation column when the analysis-target gas is passed through the separation column, and evaluating the gas in the sample bag, and the method further including the step of introducing a dilution gas into a passage connecting the separation column and the sample bag.

The third aspect of the present invention is a device for preparing a gas for odor evaluation, including:
a gas chromatograph including a separation column configured to temporally separate a plurality of components contained in an odoriferous analysis-target gas;
a timing detector configured to detect, for each of the plurality of components, the timing at which the component exits from the separation column;
a gas collector configured to collect, into a sample bag, a gas containing all or some of the components exiting from the separation column when the analysis-target gas is passed through the separation column;
a timing setter configured to allow the setting of the timing at which a component contained in the gas to be collected into the sample bag exits from the separation column; and
a gas introducer configured to introduce a dilution gas into a passage connecting the separation column and the sample bag.

Advantageous Effects of Invention

In the present invention, the components which exit from the separation column when an analysis-target gas is passed through the separation column are introduced into the gas collector along with the dilution gas. That is to say, the components which exit from the separation column are diluted with the dilution gas when passing through the passage extending from the separation column to the gas collector. This reduces the adsorption of the components to the passage. Accordingly, in a measurement of the odor of a gas collected in each sample bag, the omission of one or more components of the gas will be prevented, so that the odor of the analysis-target gas can be correctly evaluated.

BRIEF DESCRIPTION OF DRAWINGS

FIG. 4 shows the result of a test for the fragrance components of soy-sauce products of different manufacturers, where the first graph from above shows a chromatogram of a gas containing all components of a gas of soy sauce of company A, while each of the second, third and fourth graphs shows a chromatogram of a gas prepared by replacing some components of the gas of the soy sauce of company A with components of a gas of soy sauce of company B.

FIG. 5 is a table showing the odor characteristics of the fragrance components of the soy sauce of company A and those of the soy sauce of company B as well as their contributions to the fragrance formation.

FIG. 6 is a diagram showing the odor vector of the gas of the soy sauce of company A, that of the gas of the soy sauce of company B, and that of the gas prepared by replacing some components of the gas of the soy sauce of company A with components of the gas of soy sauce of company B.

DESCRIPTION OF EMBODIMENTS

An odor evaluation device as one embodiment of the present invention is hereinafter described with reference to the drawings.

<Configuration of Odor Evaluation Device>

Figure 1:
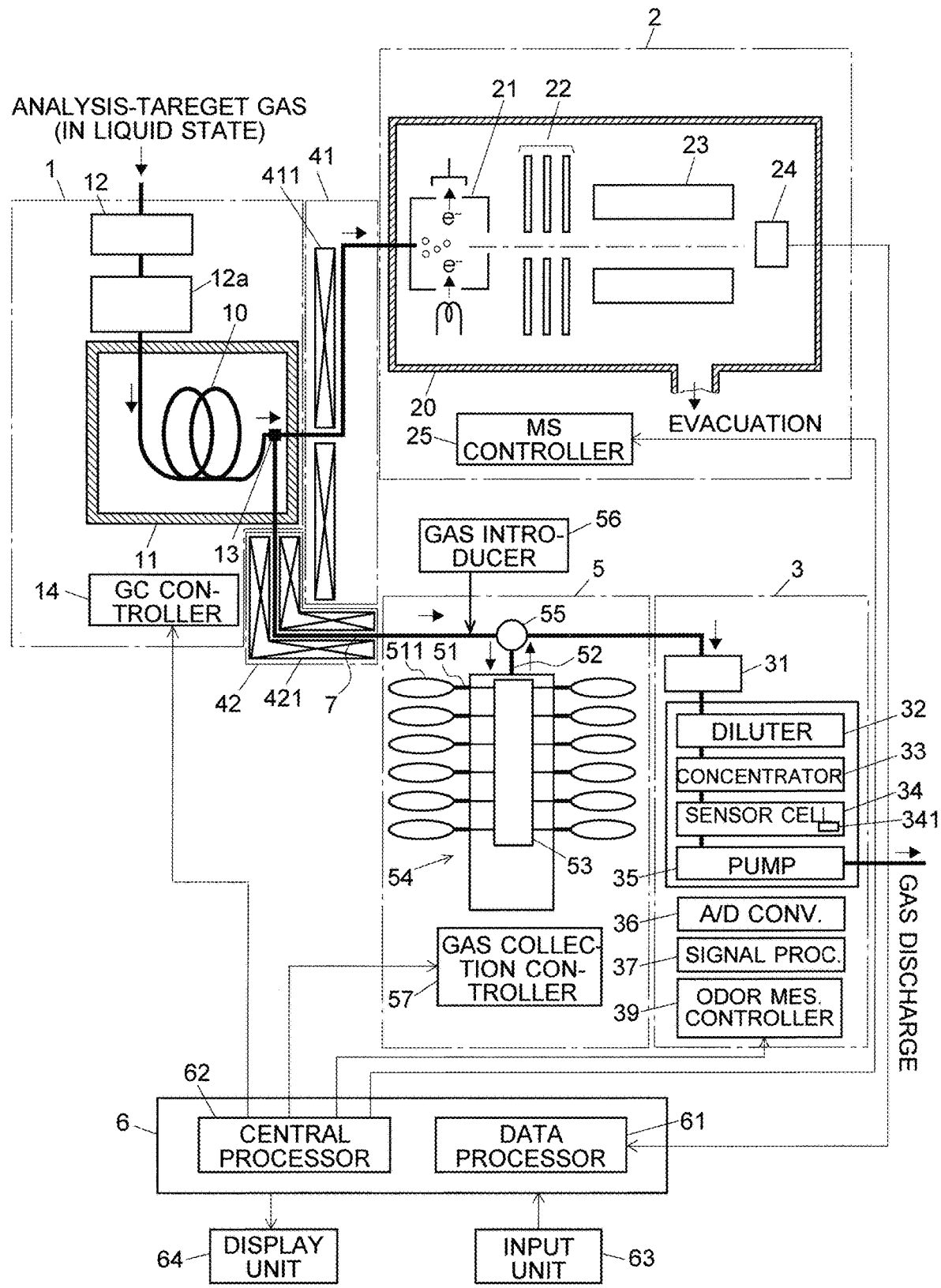
FIG. 1 is a schematic configuration diagram of an odor evaluation device according to one embodiment of the present invention.

FIG. 1 is a schematic configuration diagram of the odor evaluation device according to the present embodiment. The odor evaluation device according to the present embodiment is roughly divided into a gas chromatograph (GC) unit 1, mass spectrometry (MS) unit 2, odor measurement unit 3, interface units 41 and 42, as well as gas collection unit 5.

The GC unit 1 includes a column 10 for separating the components contained in an analysis-target gas, a column oven 11 containing the column 10, a sample injector 12 located at the entrance end of the column 10, a passage switcher 13 located at the exit end of the column 10, and a GC controller 14 configured to control those sections.

The MS unit 2 includes: a vacuum container 20; an ion source 21 configured to ionize component molecules in a gas introduced from the GC unit 1, the gas containing the components exiting from the column 10; an ion optical system 22 configured to transport the generated ions; a quadrupole mass filter 23 functioning as a mass separator configured to separate the ions according to their mass-to-charge ratios; an ion detector 24 configured to detect mass-separated ions; and an MS controller 25 configured to control those sections.

The interface unit 41, located between the GC unit 1 and the MS unit 2, includes a heater 411 for maintaining a pipeline at high temperatures to prevent the components in the gas from being trapped (adsorbed) within the passage.

The gas collection unit 5 is located between the GC unit 1 and the odor measurement unit 3, including: attachment ports 51 to which a plurality of sample bags 511 (in FIG. 1, 12 sample bags 511 are shown) are to be attached; an introduction/drawing port 52 for introducing a gas into, or drawing a gas from, the sample bags 511 attached to the attachment ports 51; an autosampler 54 including a first passage switcher 53 configured to switch the passage which connects the introduction/drawing port 52 (which corresponds to the introduction port in the present invention) to one of the attachment ports 51; a second passage switcher 55 configured to switch between the introduction/drawing port 52 and the passage connecting the GC unit 1 to the odor measurement unit 3; a gas introducer 56 configured to introduce a dilution gas into a passage 7 at a point immediately before the second passage switcher 55, the passage 7 extending from the passage switcher 13 to the second passage switcher 55; and a gas collection controller 57 configured to control the first passage switcher 53, second passage switcher 55 and gas introducer 56. The interface unit 42 is located in the passage 7 between the GC unit 1 and the gas collection unit 5, including a heater 421 for heating the passage 7 to a temperature of approximately 250 degrees Celsius, for example. It should be noted that the introduction port 52, first passage switcher 53 and second passage switcher 55 are also heated by heaters (not shown) to a temperature of approximately 250 degrees Celsius, for example. The high-temperature gas containing the components exiting from the column 10 is thereby maintained at the high temperature until it is introduced into the gas collection unit 5 and collected into a sample bag 511 along with the dilution gas.

The odor measurement unit 3 includes: a suction port 31 for drawing a gas collected in a sample bag 511 (a gas for odor evaluation, which will be described later); a diluter 32 configured to dilute the suctioned gas for odor evaluation; a concentrator 33 configured to increase the concentration of the suctioned gas; a sensor cell 34 containing a plurality of odor sensors 341 (in FIG. 1, only one of them is shown) which differ from each other in response characteristics, for the measurement of a gas for odor evaluation containing various odor components; a pump 35 for drawing the gas for odor evaluation into the sensor cell 34; an analogue-to-digital (A/D) converter 36 configured to convert detection signals produced by the odor sensors 341 into digital signals; a signal processor 37 configured to analytically process the digitized detection signals; and an odor measurement controller 39 configured to control the operation of the entire odor measurement unit 3. The diluter 32 includes a syringe and a syringe driver, for example. The syringe, which is used for diluting the gas for odor evaluation, can also serve as a pump for pushing the gas into the sensor cell 34.

As for the odor sensors 341, a metal oxide semiconductor sensor whose resistance value changes depending on the kind of odor component is typically used. Other types of sensors employing different detection mechanisms may also be used, such as a conducive polymer sensor or a sensor including a quartz resonator or surface acoustic wave (SAW) device coated with a gas adsorption film.

The signal processor 37 and the odor measurement controller 39 are constructed using a personal computer 6 as the main component. The personal computer 6 further includes, as its functions, a data processor 61 for analytically processing signals acquired with the ion detector 24 in the MS unit 2 and a central controller 62 acting as a general controller for the aforementioned controllers 14, 25, 39 and 57. An input unit 63 (e.g., keyboard and mouse) and a display unit 64 are connected to the computer 6. In the present embodiment, the MS unit 2 corresponds to the timing detector in the present invention, while the signal processor 37 corresponds to the operation processor. Furthermore, in the present embodiment, the GC unit 1, MS unit 2 and gas collection unit 5 are systematically operated when collecting gases into the sample bags 511. On the other hand, when the odor of the gases collected in the sample bags 511 is measured with the odor measurement unit 3, the gas collection unit 5 and the odor measurement unit 3 are systematically operated, with the gas collection unit 5 serving as the autosampler.

In the previous descriptions of the present embodiment, it is assumed that the GC unit 1, MS unit 2, odor measurement unit 3 and gas collection unit 5 are individually controlled by separate controllers. It is also possible, for example, to have one controller for controlling both the GC unit 1 and the MS unit 2, as well as another controller for controlling both the odor measurement unit 3 and the gas collection unit 5.

In the odor measurement unit 3, the gas components are measured as follows: When a gas which is the target of the measurement ("target gas") is introduced into the sensor cell 34, the components in the target gas come in contact with the odor sensors 341, and different detection signals are outputted from the odor sensors 314 in parallel. Those detection signals are sampled and converted into digital signals by the A/D converter 36, and sent to the signal processor 37. The signal processor 37 acquires a piece of detection data for each odor sensor 341 and for one target gas. For example, if the sensor cell 34 has ten odor sensors 341, ten pieces of detection data are obtained by a measurement of one target gas. Since the ten odor sensors 341 have different response characteristics, it is possible to consider a ten-dimensional odor space in which the outputs of the ten odor sensors 341 are respectively plotted on ten axes extending in different directions. The origin of this odor space corresponds to the state in which the outputs of all odor sensors 341 are zero.

Within the odor space, the ten pieces of detection data can be represented by a single measurement point. Now, consider an "odor vector" having the initial point at the origin of the odor space and the terminal point at a specific measurement point. The length of the odor vector corresponds to the "odor intensity" of the target gas (i.e., the concentration of the odor components in the target gas), while the direction of the odor vector corresponds to the "odor quality". That is to say, if the direction of an odor vector obtained by the measurement of one target gas is close to that of an odor vector obtained by the measurement of another target gas, the two odors can be considered to be closely related kinds of odors. Conversely, if the directions of the two vectors are significantly different, the two odors can be considered to be of distant kinds. Accordingly, as an index for determining the similarity in the direction of two vectors, the angle θ made by the two vectors can be used, and the similarity in "odor quality" can be defined based on this angle θ. For example, the similarity ratio for two odor vectors which coincide with each other (and are therefore perfectly identical in direction; i.e., when θ=0) is defined as 100%, while the similarity ratio for two odor vectors whose angle θ is equal to or larger than a predetermined value α is defined as 0%. The similarity ratio for angle θ within a range from 0 to a can be appropriately formulated depending on the angle θ.

In the case where the output level of the odor sensors 341 shows a roughly linear relationship with the concentration of the target gas (concentration of the odor components), the direction of the odor vector for odors of the same kind should always be the same and independent of their concentrations. In that case, the angle θ made by the two odor vectors will also be the same and independent of the concentration, so that a difference in odor quality among a plurality of target gases can be correctly discerned.

In the case where the output level of the odor sensors 341 shows a non-linear relationship with the concentration of the odor components, the direction of the odor vector changes depending on the concentration even when the kind of odor is the same. Therefore, it is difficult to correctly discern a difference in odor quality among a plurality of target gases. In such a case, the diluter 32 and the concentrator 33 can be regulated by a feedback control of based on the output values of the individual odor sensors 341 so that the concentration of the target gas introduced into the sensor cell 34 is constantly maintained at an appropriate level during the measurement of the target gas. Specifically, this can be achieved as follows: A measurement point which represents the detection signals from the odor sensors 341 is located within the aforementioned odor space. An odor vector having the initial point at the origin and the terminal point at the measurement point is created, and its length is calculated. The dilution ratio at the diluter 32 or concentration ratio at the concentrator 33 is controlled so that the length becomes equal to a predetermined value.

<Basic Operation of Odor Evaluation Device>

The basic operation of the odor evaluation device according to the present embodiment is hereinafter described.

A command to execute various operations using the odor evaluation device is issued through the input unit 63. Then, the GC controller 14, MS controller 25, odor measurement controller 39 and gas collection controller 57 begin to control the GC unit 1, MS unit 2, odor measurement unit 3 and gas collection unit 5, respectively, under the control of the central controller 62.

An odoriferous analysis-target gas in a gaseous or liquid state, extracted from a gaseous, liquid or solid sample, is subsequently introduced from the sample injector 12. The gas is introduced through a sample introducer 12a into the column 10. If the analysis-target gas is injected in a liquid state, the liquid is turned into vapor in the sample introducer 12a, and this vapor is pushed by a carrier gas from the sample introducer 12a into the column 10. The components in the analysis-target gas are separated from each other while passing through the column 10, and ultimately exit from the column 10 in a temporally separated form. The components which have exited from the column 10 pass through the passage switcher 13, to be introduced into either the MS unit 2 through the interface unit 41 or the gas collection unit 5 through the interface unit 42.

When the timing at which each component contained in the analysis-target gas exits from the column 10 is to be determined, all components exiting from the column 10 are introduced into the MS unit 2. Accordingly, in this situation, the passage switcher 13 is made to maintain the connection between the GC unit 1 and the MS unit 2 from the beginning of the introduction of the analysis-target gas into the column 10 until all components exit from the column 10. By this setting, the components exiting from the column 10 are sequentially introduced into the MS unit 2.

Each component introduced into the MS unit 2 is ionized by the ion source 21 under the control of the MS controller 25. Among the resulting ions, only an ion having a specific mass-to-charge ratio selected by the quadrupole mass filter 23 is allowed to reach the ion detector 24. A mass scan of a predetermined mass range is repeatedly performed in the quadrupole mass filter 23, and a series of detection signals from which a mass spectrum is to be created are acquired in the ion detector 24 in each scan.

The detection signals acquired with the ion detector 24 are processed in the data processor 61, to repeatedly create a mass spectrum with the horizontal axis representing the mass-to-charge ratio and the vertical axis representing the signal intensity. A total ion chromatogram (TIC) is also created, with the horizontal axis representing time and the vertical axis representing the signal intensity of all ions regardless of their mass-to-charge ratios. Furthermore, a mass chromatogram focused on a specific mass-to-charge ratio is also created, with the horizontal axis representing time and the vertical axis representing the signal intensity at the mass-to-charge ratio concerned. Although creating a TIC is sufficient for detecting the timing at which each component exits from the column 10, a mass spectrum or mass chromatogram may also be created as needed. The data of the TIC created by the data processor 61 is stored in the same data processor 61. Additionally, the data processor 61 detects each peak on the created TIC and stores information concerning the peak, such as the peak intensity, peak area and peak width (time range).

Figure 2:
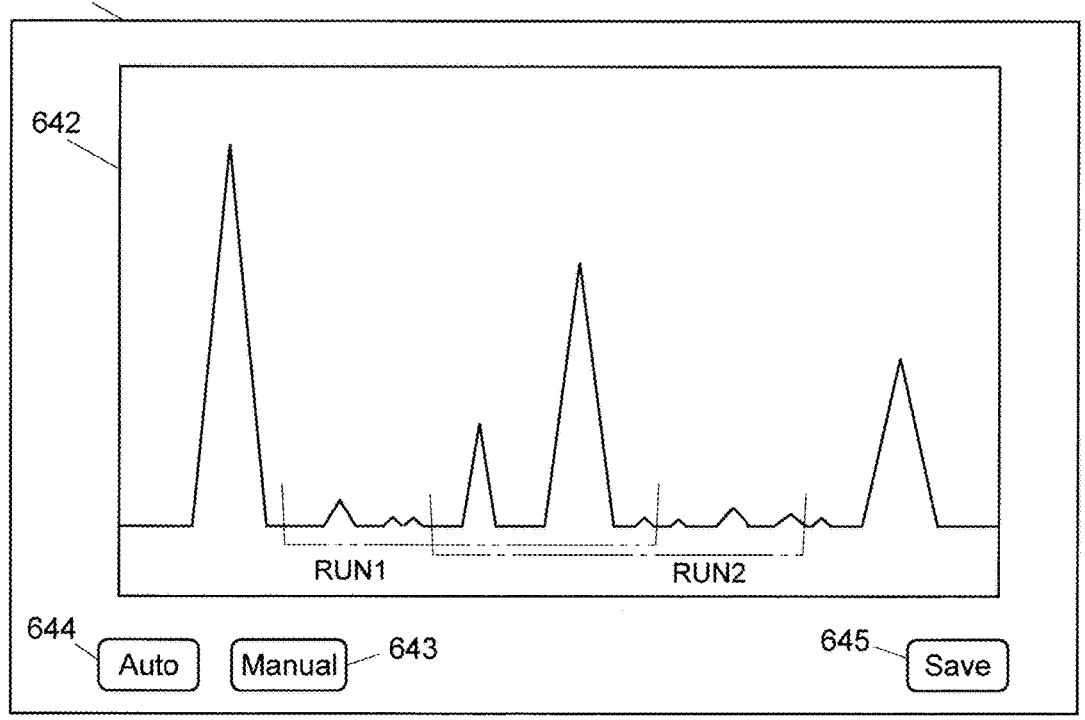
FIG. 2 is a diagram showing one example of the display screen.

Additionally, the TIC created by the data processor 61 is drawn on the display screen of the display unit 64. FIG. 2 shows one example of the display screen 641 on which a TIC is displayed.

In the present embodiment, the display screen 641 doubles as a screen for setting a time range (retention time range, or RT range) within which a component or components that should be excluded from the components to be collected into a sample bag 511 will exit from the column 10. The data processor 61 automatically sets the timing to switch the passage switcher 13 to the state in which the GC unit 1 is connected to the gas collector 5, and the identification number of the sample bag 511 into which the component or components exiting from the column 10 at that timing should be collected, so that all components except for those which correspond to the previously set time range will be collected into the designated sample bag 511.

The time range within which the component or components to be excluded (or omitted) from the entire group of components exit from the column 10 is set either by a manual operation or automatically. For the manual setting of the time range, for example, the user clicks the "Manual" button 643 on the display screen 641 with the mouse cursor and specifies a desired time range on the TIC 642 with the cursor. In the example shown in FIG. 2, two ranges of time labeled "RUN1" and "RUN2" have been set on the TIC 642.

After the time ranges have been thus set, the operation of collecting gases into the sample bags 511 is performed as follows: Initially, the passage switcher 13 is controlled so as to switch the passage so that that the GC unit 1 is not connected to the gas collection unit 5 during the time range designated as "RUN1", while the GC unit 1 is connected to the gas collection unit 5 during the other time ranges (first gas-collecting operation). Subsequently, the passage switcher 13 is controlled so as to switch the passage so that the GC unit 1 is not connected to the gas collection unit 5 during the time range designated as "RUN2", while the GC unit 1 is connected to the gas collection unit 5 during the other time ranges (second gas-collecting operation). The first and second gas-collecting operations use different sample bags 511 to collect a component or components. By the present operation, a component or components which do not form a peak on the TIC due to their low concentration or low detection sensitivity can be selectively collected into a sample bag 511 or excluded from the component or components to be collected into a sample bag 511.

Figure 3:
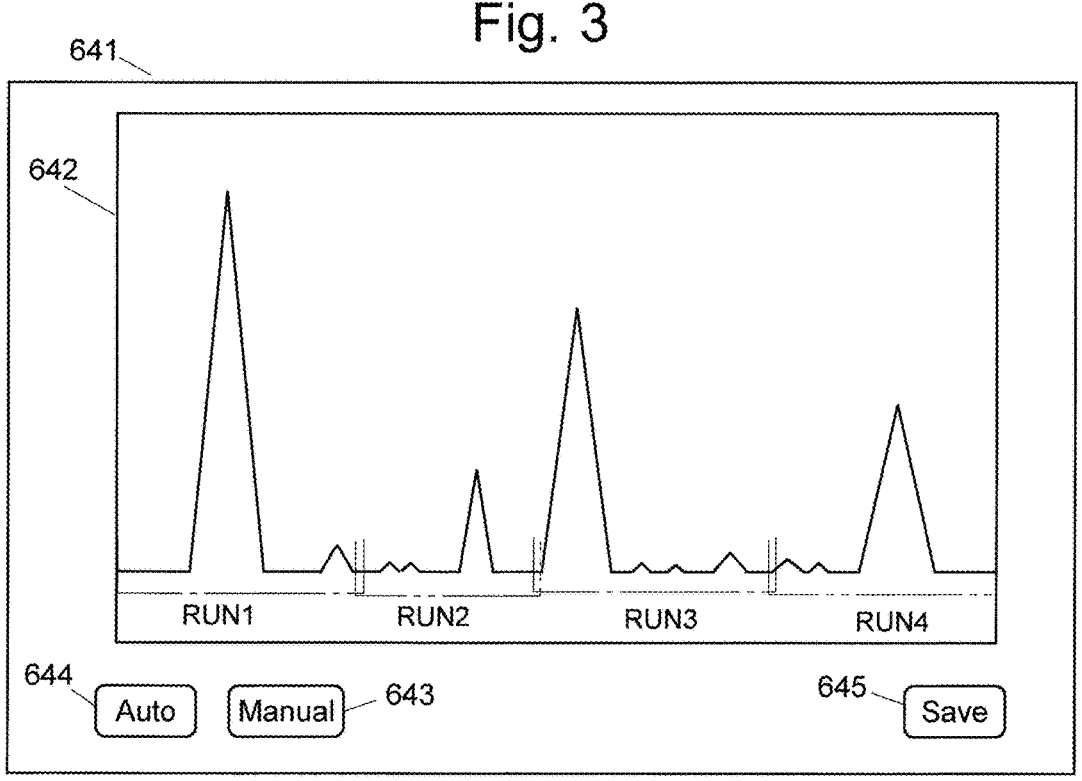
FIG. 3 is a diagram showing another example of the display screen.

On the other hand, FIG. 3 shows an example of the display screen 641 in the case where the time range during which the component or components that should be excluded from the entire group of components exit from the column 10 has been automatically set. The automatic setting is initiated, for example, by clicking the "Auto" button 644 on the display screen 641 with the mouse cursor. The data processor 61 sets a plurality of time ranges by automatically dividing the entire time range of the TIC 642. In FIG. 3, four ranges of time labeled RUN1 through RUN4 are set. As a basic rule, the data processor 61 sets time ranges by equally dividing the TIC 642, and if the beginning or ending period of a time range is located on a peak whose intensity or width exceeds a predetermined value, the setting of the time range in question should be changed so that the beginning or ending period will not be within the peak. That is to say, the automatic setting means an automatic setting of the timing at which the component or components that should be excluded from the components to be collected into a sample bag 511 exit from the column 10.

The contents of the automatic or manual setting (i.e., the timing at which the component or components that should be excluded from the components to be collected into a sample bag 511 exit from the column 10, as well as the information concerning the number of sample bags and other related conditions) will be saved in the data processor 61 when the "Save" button 645 displayed in the lower right section of the display screen 641 is clicked with the mouse (or the like).

Thus, the display unit 64 (display screen 641), input unit 63, data processor 61 and central controller 62 function as the timing setter in the present invention.

In the case of preparing an "gas for odor evaluation" which is a gas for measuring the odor of a component or components contained in an analysis-target gas, all or some of the components exiting from the column 10 are introduced into the gas collection unit 5. That is to say, under the control of the GC controller 14 and the gas collection controller 57, the drive motor for the passage switcher 13 as well as the first and second passage switchers 53 and 55 are operated so as to establish either the state in which the GC unit 1 is connected to the MS unit 2 or the state in which the GC unit 1 is connected to the gas collection unit 5 according the contents of the automatic or manual setting stored in the data processor 61. By this operation, the component or components exiting from the column 10 at the predetermined timing are introduced into the gas collection unit 5 and collected into a sample bag 511 having a specified identification number.

When the passage switcher 13 is in the state of connecting the GC unit 1 to the gas collection unit 5, a dilution gas is supplied from the gas introducer 56 into the passage 7 between the passage switcher 13 and the second passage switcher 55. Thus, along with the component or components coming from the column 10, the dilution gas is collected into the sample bag 511.

As for the dilution gas, an odorless or nearly odorless gas which does not affect the odor of each component to be introduced into the gas collection unit should be used, such as nitrogen or helium.

The dilution gas additionally acts as a cleaner of the passage in the gas collection unit 5. Therefore, it is preferable to always supply the dilution gas into the passage 7 regardless of whether or not the gas from the GC unit 1 is flowing in the passage 7. However, the supply of the dilution gas into the passage 7 may be limited to the period of time when the gas from the GC unit 1 is flowing in the passage 7. Furthermore, the supply of the dilution gas may be avoided even when the component or components exiting from the column 10 are being introduced into the gas collection unit 5.

Thus, a gas for odor evaluation which contains all or some of the components exiting from the column 10 when an analysis-target gas is introduced into the column 10 is collected into a sample bag 511. A plurality of kinds of gases for odor evaluation can be individually collected in separate sample bags 511. After a gas for odor evaluation which contains all or some of the components exiting from the column 10 when an analysis-target gas is introduced into the column 10 has been collected in a specified sample bag 511, a gas which contains all or some of the components exiting from the column 10 when another analysis-target gas that is different from the aforementioned analysis-target gas is introduced into the column 10 can additionally be collected in the same specified sample bag 511. By this operation, a gas for odor evaluation composed of a plurality of components originally contained in two or more kinds of analysis-target gases is prepared.

An operation in which the odor of each of the gases for odor evaluation collected in the sample bags 511 is measured by the odor measurement unit 3 is as follows.

The passages in the first and second passage switchers 53 and 55 are changed under the control of the gas collection controller 57. The gases for odor evaluation are sequentially drawn from the sample bags 511 in the gas collection unit 5 into the sensor cell 34 by the pump 35 under the control of the odor measurement controller 39. The component or components contained in the gas for odor evaluation come in contact with each of the odor sensors 341, whereupon each odor sensor 341 outputs a detection signal. In place of the pump 35, the syringe in the diluter 32 can be used to draw a gas for odor evaluation from a sample bag 511 and subsequently push the same gas toward the odor sensors 341.

Based on the detection signals from the odor measurement unit 3, the data processor 61 creates an odor vector which represents the detection result of each gas for odor evaluation within an odor space (e.g., a ten-dimensional space). Based on the odor vectors of the gases for odor evaluation, the data processor 61 calculates an index value representing the similarity between the gases for odor evaluation and displays the calculated result on the display unit 64. For this display, the data processor 61 may allow the user to select the kinds of gases for odor evaluation for which the index value should be calculated, or the kinds of gases for odor evaluation whose index values should be displayed on the display unit 64. Additionally, the output values of the odor sensors 341 for each gas for odor evaluation may also be displayed on the display unit 64.

A sniffing port (not shown) can be connected to each attachment port 51 in place of the sample bag 511 to allow a plurality of individuals in charge of odor evaluation to perform a sensory test of the same gas using a plurality of ports of the gas collection unit 5. It is also possible to temporarily collect gases in the sample bags 511 and subsequently perform a sensory test. For example, a triangle odor bag method, which is one of the sensory testing methods, can be used when comparing the odor of a gas which contains the component or components collected in a sample bag 511 (gas for odor evaluation) with the odor of the analysis-target gas.

SPECIFIC EXAMPLES

Hereinafter shown are examples of the preparation of a gas for odor evaluation and examples of the use of a gas for odor evaluation collected in a sample bag 511.

(1) An analysis-target gas is introduced into the column 10. Among all components exiting from the column 10, only the component or components exiting from the column at a predetermined timing are collected into a sample bag 511 as a gas for odor evaluation.

This gas for odor evaluation is useful, for example, for determining the odor quality of each component contained in the analysis-target gas, or for evaluating the odor intensity of each component.

(2) An analysis-target gas is introduced into the column 10. Among all components exiting from the column 10, only the component or components exiting from the column at a predetermined timing are excluded, leaving the other component or components to be collected into a sample bag 511 as the gas for odor evaluation.

This gas for odor evaluation is useful, for example, for identifying the minimal set of components which form the odor of the analysis-target gas, or for correctly evaluating the odor of the target components contained in the analysis-target gas.

When the odor of one gas for odor evaluation has been identified as being close to that of the analysis-target gas by the triangle odor bag method (or other methods), it is possible to conclude that no important component for the odor formation of the analysis-target gas is included in the component or components excluded (omitted) from that gas for odor evaluation.

It is said that humans have 400 olfactory receptors for selecting and identifying odors. Accordingly, more than 400 sensors are actually required for an odor-identifying device, or an electronic nose or similar device intended to substitute for the human olfactory organ, to be responsive to not only a specific odor quality but also various odor qualities, and to be capable of selecting and identifying all kinds of odor qualities which humans can sniff out. However, preparing as many as 400 sensors is unreasonable and impractical for the current level of technology. On the other hand, a difference between the odors of a specific kind (e.g., a difference in odor depending on the kind of flower) can be achieved by as few as ten sensors. However, if a totally different kind of odor (e.g., the odor of milk) is mixed in the odor of interest, that foreign odor interferes with the response of the sensor, making it difficult to identify the target odor. By comparison, the odor evaluation device according to the previous embodiment can prepare a gas for odor evaluation which contains the components of the analysis-target gas while excluding the components that will interfere with the evaluation of the odor of the analysis-target gas (interfering components). Accordingly, the odor of the analysis-target gas can be satisfactorily identified with as few as ten sensors. An example of the interfering component is the solvent component (toluene) of a bathroom deodorant contained in an analysis-target gas sampled from the air in a bathroom in order to measure the odor of the bad smell from the toilet. When the analysis-target gas is a citrus fragrance, an amount of limonene excessively contained in the fragrance will be an interfering component.

(3) An analysis-target gas is introduced into the column 10, and all components exiting from the column 10 are collected into a sample bag 511. Subsequently, the analysis-target gas is once more introduced into the column 10. This time, the component or components which exit from the column 10 at a predetermined timing are excluded, and the other component or components are collected into the same sample bag 511 as the aforementioned one. By varying the number of times of the collection of all components into the sample bag 511 and that of the times of the collection of the components exclusive of some components, a plurality of gases for odor evaluation with different component ratios can be prepared. The concentration of the components in the gas for odor evaluation collected in the sample bag 511 can also be varied by changing the amount of dilution gas introduced into the gas collection unit 5 along with the components exiting from the column 10.

Two different kinds of analysis-target gases may be successively introduced into the column 10 (which are hereinafter referred to as the first and second gases). In that case, a gas for odor evaluation containing all components of the first gas and some components of the second gas can be prepared. For example, this gas for odor evaluation is useful for determining which component has the masking effect on a specific kind of bad smell (which corresponds to the first gas) among the components in a gas which has the masking effect (a masking gas, which corresponds to the second gas).

More specifically, two gases for odor evaluation can be prepared, one of which is a mixture of the bad smell and the masking gas from which a component or components have been excluded, and the other is a mixture of the bad smell and the masking gas containing all of its components. If the former gas exhibits a decrease in masking effect as compared to the latter, the component or components excluded from the masking gas can be identified as the component or components producing the masking effect. That is to say, which component or components are minimally required for the masking can be determined.

(4) One analysis-target gas (first gas) is initially introduced into the column 10. Among all components exiting from the column 10, only the component or components which exit from the column 10 at a predetermined timing (RT range) are collected into a sample bag 511. Subsequently, another analysis-target gas (second gas) different from the first analysis-target gas is introduced into the column 10. Among all components exiting from the column 10, the component or components which exit from the column 10 at the timings except for the aforementioned RT range are collected into the same sample bag 511. By this operation, a gas for odor evaluation is prepared which contains the components of the second gas among which the component or components that exit from the column at the predetermined timing are replaced by the component or components of the first gas that exit from the column 10 at the predetermined timing.

This gas for odor evaluation is useful for identifying a component or components which determine the difference in odor between two kinds of gases having slightly different odors or a component or components which have a masking effect, or for investigating a change in odor quality.

For example, a plurality of gases for odor evaluation are prepared using different timings at which the component or components that should be replaced between the first and second gases exit from the column 10. For each of the plurality of gases for odor evaluation, the degree of similarity to the first gas is determined. If the degree of similarity between a gas for odor evaluation and the first gas is higher than the degree of similarity between the first and second gases, it is possible to conclude that the component or components replaced in the gas for odor evaluation are the component or components that determine the difference in odor between the first and second gases.

Hereinafter described are the results of an experiment in which specific food products were tested for an odor component or components.

The test specimens were two products of soy sauce having different odor qualities, manufactured by companies A and B. The aromatic components of both soy-sauce products of companies A and B had already been completely identified. However, the component or components which produce their difference in odor quality had not yet been known.

The first graph from above in FIG. 4 shows a chromatogram of a gas (odor components) emitted from the soy sauce of company A. The second, third and fourth graphs in FIG. 4 respectively correspond to the following three cases: (Case 1) a chromatogram of a gas (gas for odor evaluation) obtained by an operation in which the gas of the soy sauce of company A corresponding to the first section of the RT range of the first chromatogram was replaced with that of the soy sauce of company B; (Case 2) a chromatogram of a gas for odor evaluation obtained by an operation in which the gas of the soy sauce of company A corresponding to the second section of the RT range of the first chromatogram was replaced with that of the soy sauce of company B; and (Case 3) a chromatogram of a gas for odor evaluation obtained by an operation in which the gas of the soy sauce of company A corresponding to the last section of the RT range of the first chromatogram was replaced with that of the soy sauce of company B.

The gases for odor evaluation in Cases 1 and 2 did not have the odor of the soy sauce of company B, whereas the gas for odor evaluation in Case 3 had almost the same odor as that of the soy sauce of company B as a result of the replacement of the odor components. From these results, it is possible to consider that the components corresponding to the second half of the RT range of the chromatogram of the soy sauce of company A include an important aromatic component or components which determine the difference in fragrance between the soy-sauce products of companies A and B (in other words, replacing those components with the corresponding components of the soy sauce of company B changes the odor of the soy sauce of company A to that of the soy sauce of company B). Based on this finding, a detailed investigation was conducted for the component or components corresponding to the second half of the RT range of the chromatogram of the soy sauce of company A. The result was as shown in FIG. 5.

FIG. 5 shows the result of a sensory test which was performed using the odor evaluation device according to the present embodiment to investigate what type of odor each of the component or components has within a considerably narrow RT range. In FIG. 5, the components indicated by the thin arrows were initially considered to be decisive components for the fragrance of the soy sauce due to their high levels of odor intensity and their odor qualities. However, replacing those components did not change the odor of the soy sauce of company A to that of the soy sauce of company B. Taking this result into account, various components were replaced in a systematic way, which revealed that replacing the components indicated by the thick arrows in FIG. 5 changes the odor of the soy sauce of company A to that of the soy sauce of company B. This result almost identical to that of a sensory test using a normal type of sniffer GC.

What is noteworthy in the aforementioned result is the fact that each of the components indicated by the thick arrows was almost odorless when tested independently. That is to say, replacing the almost odorless components of the soy sauce of company A with the corresponding components of the soy sauce of company B changed the odor of the soy sauce of company A to that of the soy sauce of company B. To confirm this result, the similarity of the soy sauce of company A, the soy sauce of company B, and the soy sauce of company A after the replacement of the components in question, was investigated by the odor measurement unit 3. The result was as shown in FIG. 6. The odor measurement unit 3 is essentially a type of device commonly known as an "odor identification device". In FIG. 6, the vector labeled "A" is the measured vector of the fragrance of the soy sauce of company A, and the vector labeled "B" is the measured vector of the fragrance of the soy sauce of company B. The vector labeled "C" is the measured vector of the fragrance of the soy sauce of company A after the components indicated by the thick arrows in FIG. 5 were replaced with the corresponding components of the soy sauce of company B. With the angle made by vectors A and B defined as 100%, the angle made by vectors A and C was 76%. That is to say, the fragrance of the soy sauce of company A after the replacement of the components indicated by the thick arrows had a similarity of 76% to the fragrance of the soy sauce of company B. It is often difficult for the odor measurement unit 3 to satisfactorily measure the odor of a food product which contains a considerable amount of ethanol, like soy sauce. By contrast, the odor evaluation device according to the present embodiment can yield a satisfactory result comparable to the result obtained by a sensory test since the interfering components originating from ethanol can be removed.

(5) The gas for odor evaluation collected in a sample bag 511 can be used not only for a measurement in the odor measurement unit 3 but also for an analysis using the GCMS. For example, although a gas for odor evaluation should normally contain the intended kinds of components, it is actually possible that some components are lost for some reasons, such as thermal decomposition or vaporization before the gas for odor evaluation is prepared. In such a case, it is preferable to perform a GCMS analysis of the gas for odor evaluation collected in the sample bag 511 to check for the components contained in the gas for odor evaluation. In the present embodiment, since the gas for odor evaluation is contained in the sample bag 511, the GCMS analysis of the gas for odor evaluation can be performed even after the measurement of the gas has been completed.

Figure 7:
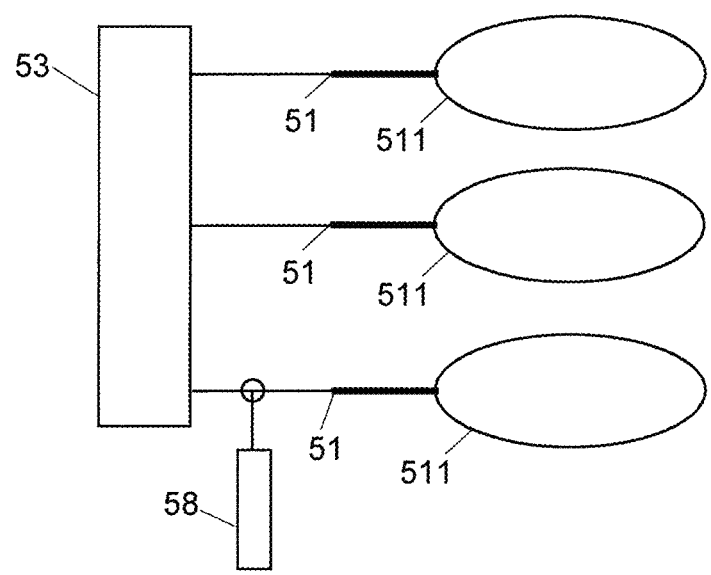
FIG. 7 is a diagram showing a configuration example in which a collecting tube is connected to the passage leading to an attachment port of a gas collection unit.

As another possibility, as shown in FIG. 7, a removable collecting tube 58 may be connected via a switching valve to a branch of the passage between the first passage switcher 53 and an attachment port 51. By appropriately the passage with the switching valve, the gas for odor evaluation can be collected into the collecting tube 58 and not the sample bag 511. According to this configuration, the components collected in the collecting tube 58 (i.e., the components of the gas for odor evaluation collected in the sample bag 511) can be conveniently analyzed by removing the collecting tube 58 from the branch and attaching it to the sample-injecting unit of the GCMS device. Even a component which adsorbs to the sample bag 511 and cannot be retrieved from the bag can be collected and analyzed by using the collecting tube 58. As the collecting tube 58, for example, a Tenax® collection tube containing a sorbent for adsorbing gas components can be used.

(6) As already described, the gas for odor evaluation collected in a sample bag 511 can be used not only for an odor measurement in the odor measurement unit 3 but also for sensory evaluation using the human olfactory sense.

When a normal type of sniffing GC is sniffed by a plurality of individuals, the pipe extending from the exit port of the GC to the sniffing area needs to be separated into the same number of branches as the individuals, which makes the system complex. Furthermore, all of the individuals need to concentrate on the timing at which each component exits from the exit port of the GC, so as to avoid missing the component. By comparison, the device according to the present embodiment allows sniffing ports to be connected to a plurality of attachment ports 51 in the collection unit 5 and thereby enable the device to serve as a sniffing GC. Furthermore, a gas containing a component or components exiting from the column within a certain period of time as shown in FIG. 5 is temporarily collected into a sample bag, allowing the user to unhurriedly sniff the gas later. The device also allows a plurality of individuals to sniff the same sample.

[Aspects of Invention]

A person skilled in the art can understand that the previously described embodiment is a specific example of the following aspects of the present invention.

(Clause 1) The first aspect of the present invention is an odor evaluation device, including:
   a gas chromatograph including a separation column configured to temporally separate a plurality of components contained in an odoriferous analysis-target gas;
   a timing detector configured to detect, for each of the plurality of components, the timing at which the component exits from the separation column;
   a gas collector configured to collect, into a sample bag, a gas containing all or some of the components exiting from the separation column when the analysis-target gas is passed through the separation column;
   a timing setter configured to allow the setting of the timing at which a component contained in the gas to be collected into the sample bag exits from the separation column; and
   a gas introducer configured to introduce a dilution gas into a passage connecting the separation column and the sample bag.

In the odor evaluation device described in Clause 1, when a gas containing all or some of the components contained in an analysis-target gas is collected into a sample bag, a dilution gas is supplied into the passage connecting the separation column and the sample bag, whereby the adsorption of the components to the passage is prevented. This prevents unnecessary components from being mixed into the gas to be collected into the sample bag. In normal cases, the concentration of the analysis-target gas to be introduced into the gas chromatograph is previously increased by a preprocessing so that the components contained in the gas which will exit from the separation column will have appropriate concentrations for the MS analysis. By using the dilution gas, the components contained in the gas to be collected into the sample bag can be restored to their original concentrations.

(Clause 2) In the odor evaluation device described in Clause 2, which is one mode of the odor evaluation device described in Clause 1, the gas collector includes: a plurality of attachment ports to which sample bags are to be attached; an introduction port for introducing a gas containing all or some of the components exiting from the separation column into each of the sample bags respectively attached to the plurality of attachment ports; and a passage switcher configured to switch a passage connecting the plurality of attachment ports and the introduction port.

By the odor evaluation device described in Clause 2, a gas to be used for the odor evaluation of an analysis-target gas can be collected into each of the sample bags. The gases individually collected in the plurality of sample bags can be collectively subjected to an odor measurement.

(Clause 3) In the odor evaluation device described in Clause 3, which is one mode of the odor evaluation device described in Clause 1 or 2, the timing detector is a mass analyzer.

The timing detector only needs to be capable of determining the timing at which a component contained in an analysis-target gas exits from the separation column. Accordingly, a flame ionization detector (FID), which is a standard detector for gas chromatographs, may also be used. Using a mass analyzer as the timing detector as in the odor evaluation device described in Clause 3 enables the identification of each component along with the detection of the timing at which the component exits from the separation column The "timing at which the component exits from the separation column" in the present context means, for example, the beginning period, beginning and ending periods, or beginning period and a time range, at or during which a component exits from the separation column (Clause 4) The odor evaluation device described in Clause 4, which is one mode of the odor evaluation device described in one of Clauses 1-3, further includes an odor measurement section including a plurality of odor sensors which differ from each other in response characteristics, for measuring the odor of the gas in the sample bag.

The odor evaluation device described in Clause 4 can introduce the gas collected in the sample bag into the odor measurement section and measure its odor, without requiring the sample bag to be removed from the gas collector.

(Clause 5) In the odor evaluation device described in Clause 5, which is one mode of the odor evaluation device described in one of Clause 1, the gas collector includes an attachment port to which a sample bag is to be attached, and the odor evaluation device further includes a sniffing port to be connected to the attachment port.

Conventional sniffing GCs require a user to sniff a component and perform a sensory test at the exact point in time where the component exits from the separation column. In the odor evaluation device described in Clause 5, a gas containing a component exiting from the separation column during a specific period of time can be temporarily collected in the sample bag, thereby allowing a user to unhurriedly sniff the gas in the sample bag at a later point in time and perform a sensory test. The device also allows a plurality of individuals to sniff the gas collected in the same sample bag and perform a sensory test.

(Clause 6) The odor evaluation device described in Clause 6, which is one mode of the odor evaluation device described in one of Clause 1, further includes a controller configured to control the gas collector so as to collect, into the sample bag or one of sample bags provided in the gas collector, all components exiting from the separation column of the gas chromatograph when a first analysis-target gas is passed through the separation column, and a component exiting from the separation column at a predetermined timing among the components exiting from the separation column of the gas chromatograph when a second analysis-target gas is passed through the separation column, where the kind of the second analysis-target gas is the same as or different from the kind of the first analysis-target gas.

(Clause 7) The odor evaluation device described in Clause 7, which is one mode of the odor evaluation device described in one of Clause 1, further includes a controller configured to control the gas collector so as to collect, into the sample bag or one of sample bags provided in the gas collector, a component exiting from the separation column of the gas chromatograph at a predetermined timing among the components exiting from the separation column when a first analysis-target gas is passed through the separation column, and a component exiting from the separation column within a time range exclusive of the predetermined timing among the components exiting from the separation column when a second analysis-target gas which is different from the first analysis-target gas is passed through the separation column (Clause 8) The odor evaluation device described in Clause 8, which is one mode of the odor evaluation device described in one of Clause 1, further includes a controller configured to control the gas collector so as to collect, into a sample bag in which a predetermined gas is contained beforehand among the sample bags provided in the gas collector, a component exiting from the separation column of the gas chromatograph within a time range exclusive of a predetermined timing among the components exiting from the separation column when an analysis-target gas is passed through the separation column The odor evaluation devices described in Clauses 6-8 can prepare various kinds of gases for the evaluation of an analysis-target gas, such as a gas in which all components of the analysis-target gas are mixed at a different ratio from the original analysis-target gas, or a gas which contains all components of an analysis-target gas exclusive of some specific components, or a gas in which all or some of the components contained in different kinds of analysis-target gases are mixed. In other words, it is possible to prepare an appropriate gas from an analysis-target gas by removing a component that affects the measurement of the odor of the analysis-target gas from the components contained in the analysis-target gas, or by increasing or decreasing the mixture ratio of a specific component (i.e., concentrating or diluting a specific component) among the components contained in the analysis-target gas.

(Clause 9) The second aspect of the present invention is an odor evaluation method including the steps of passing an odoriferous analysis-target gas through a separation column of a gas chromatograph, collecting, into a sample bag, a gas containing all or some of the components exiting from the separation column when the analysis-target gas is passed through the separation column, and evaluating the gas in the sample bag, and the method further including the step of introducing a dilution gas into a passage connecting the separation column and the sample bag.

(Clause 10) The odor evaluation method described in Clause 10, which is one mode of the odor evaluation method described in Clause 9, further includes the step of collecting, into the sample bag, all components exiting from the separation column of the gas chromatograph when a first analysis-target gas is passed through the separation column, and a component exiting from the separation column at a predetermined timing among the components exiting from the separation column of the gas chromatograph when a second analysis-target gas is passed through the separation column, where the kind of the second analysis-target gas is the same as or different from the kind of the first analysis-target gas.

(Clause 11) The odor evaluation method described in Clause 11, which is one mode of the odor evaluation method described in Clause 9, further includes the step of collecting, into the sample bag, a component exiting from the separation column of the gas chromatograph at a predetermined timing among the components exiting from the separation column when a first analysis-target gas is passed through the separation column, and a component exiting from the separation column within a time range exclusive of the predetermined timing among the components exiting from the separation column when a second analysis-target gas which is different from the first analysis-target gas is passed through the separation column (Clause 12) The odor evaluation method described in Clause 12, which is one mode of the odor evaluation method described in Clause 9, further includes the step of collecting, into the sample bag in which a predetermined gas is contained beforehand, a component exiting from the separation column of the gas chromatograph within a time range exclusive of a predetermined timing among the components exiting from the separation column when an analysis-target gas is passed through the separation column (Clause 13) The odor evaluation method described in Clause 13, which is one mode of the odor evaluation method described in one of Clauses 9-12, further includes the step of measuring the odor of the gas in the sample bag by using an odor measurement device including m odor sensors which differ from each other in response characteristics, where m is an integer equal to or greater than two.

(Clause 14) The odor evaluation method described in Clause 14, which is one mode of the odor evaluation method described in one of Clauses 9-12, further includes the step of evaluating the odor of the gas in the sample bag by a sensory test using an olfactory sense.

(Clause 15) The third aspect of the present invention is a device for preparing a gas for odor evaluation, including:
  a gas chromatograph including a separation column configured to temporally separate a plurality of components contained in an odoriferous analysis-target gas;
  a timing detector configured to detect, for each of the plurality of components, the timing at which the component exits from the separation column;
  a gas collector configured to collect, into a sample bag, a gas containing all or some of the components exiting from the separation column when the analysis-target gas is passed through the separation column;
  a timing setter configured to allow the setting of the timing at which a component contained in the gas to be collected into the sample bag exits from the separation column; and
  a gas introducer configured to introduce a dilution gas into a passage connecting the separation column and the sample bag.

In the device for preparing a gas for odor evaluation described in Clause 15, when a gas containing all or some of the components contained in an analysis-target gas is collected into a sample bag, a dilution gas is supplied into the passage connecting the separation column and the sample bag, whereby the adsorption of the components to the passage is prevented. Therefore, unnecessary components are prevented from being mixed into the gas to be collected into the sample bag, so that a useful or necessary gas for evaluating the odor of the analysis-target gas can be prepared.

REFERENCE SIGNS LIST

1 . . . Gas Chromatograph (GC) Unit
10 . . . Column
12 . . . Sample Injector
13 . . . Passage Switcher
14 . . . GC Controller
2 . . . Mass Spectrometry (MS) Unit
25 . . . MS Controller
3 . . . Odor Measurement Unit 31 ... Suction Port
34 ... Sensor Cell
341 ... Odor Sensor
36 ... Analogue-to-Digital (A/D) Converter
37 ... Signal Processor
39 ... Odor Measurement Controller
41, 42 ... Interface Unit
411, 421 ... Heater
5 ... Gas Collection Unit
51 ... Attachment Port
511 ... Sample Bag
52 ... Introduction/Drawing Port
53 ... First Passage Switcher
54 ... Autosampler
55 ... Second Passage Switcher
56 ... Gas Introducer
57 ... Gas Collection Controller
58 ... Collecting Tube
6 ... Personal Computer
61 ... Data Processor
62 ... Central Controller
63 ... Input Unit
64 ... Display Unit
641 ... Display Screen
642 ... Total Ion Chromatogram (TIC)

The invention claimed is:

1. An odor evaluation device, comprising:
a gas chromatograph including a separation column configured to temporally separate a plurality of components contained in an odoriferous analysis-target gas;
a first passage into which the plurality of components exiting from the separation column are introduced;
a timing detector configured to detect, for each of the plurality of components, a timing at which the component exits from the separation column;
a gas collector including an attachment port to which a sample bag is to be attached and a passage switcher configured to switch a condition of connecting the first passage and the attachment port, and configured to collect, into the sample bag, a gas containing all or some of the components exiting from the separation column when the analysis-target gas is passed through the separation column;
a timing setter configured to set a timing at which a component contained in the gas to be collected into the sample bag exits from the separation column based on a detection result of the timing detector; and
a second passage connected to the first passage at a position between the separation column and the passage switcher;
a gas introducer connected to the second passage and configured to introduce a dilution gas into the second passage.

2. The odor evaluation device according to claim 1, wherein the gas collector includes: a plurality of attachment ports to which sample bags are to be attached, and an introduction port for introducing the gas containing all or some of the components exiting from the separation column into each of the sample bags respectively attached to the plurality of attachment ports; and
wherein the passage switcher configured to switch a passage connecting the plurality of attachment ports and the introduction port.

3. The odor evaluation device according to claim 1, wherein the timing detector is a mass analyzer.

4. The odor evaluation device according to claim 1, further comprising an odor measurement section including a plurality of odor sensors which differ from each other in response characteristics, for measuring an odor of the gas in the sample bag.

5. The odor evaluation device according to claim 1, wherein:
the gas collector includes an attachment port to which a sample bag is to be attached; and
the odor evaluation device includes a sniffing port to be connected to the attachment port.

6. The odor evaluation device according to claim 1, further comprising a controller configured to control the gas collector so as to collect, into the sample bag or one of sample bags provided in the gas collector, all components exiting from the separation column of the gas chromatograph when a first analysis-target gas is passed through the separation column, and a component exiting from the separation column at a predetermined timing among the components exiting from the separation column of the gas chromatograph when a second analysis-target gas is passed through the separation column, where a kind of the second analysis-target gas is a same as or different from a kind of the first analysis-target gas.

7. The odor evaluation device according to claim 1, further comprising a controller configured to control the gas collector so as to collect, into the sample bag or one of sample bags provided in the gas collector, a component exiting from the separation column of the gas chromatograph at a predetermined timing among the components exiting from the separation column when a first analysis-target gas is passed through the separation column, and a component exiting from the separation column within a time range exclusive of the predetermined timing among the components exiting from the separation column when a second analysis-target gas which is different from the first analysis-target gas is passed through the separation column.

8. The odor evaluation device according to claim 1, further comprising a controller configured to control the gas collector so as to collect, into a sample bag in which a predetermined gas is contained beforehand among the sample bags provided in the gas collector, a component exiting from the separation column of the gas chromatograph within a time range exclusive of a predetermined timing among the components exiting from the separation column when an analysis-target gas is passed through the separation column.

9. An odor evaluation method including steps of passing an odoriferous analysis-target gas through a separation column of a gas chromatograph, collecting, into a sample bag, a gas containing all or some of components exiting from the separation column when the analysis-target gas is passed through the separation column, and evaluating the gas in the sample bag, the method comprising:
a step of introducing a dilution gas into a second passage connected to a first passage connecting the separation column and the sample bag, the second passage connected to the first passage at a position between the separation column and the sample bag.

10. The odor evaluation method according to claim 9, further comprising a step of collecting, into the sample bag, all components exiting from the separation column of the gas chromatograph when a first analysis-target gas is passed through the separation column, and a component exiting from the separation column at a predetermined timing among components exiting from the separation column of the gas chromatograph when a second analysis-target gas is passed through the separation column, where a kind of the second analysis-target gas is a same as or different from a kind of the first analysis-target gas.

11. The odor evaluation method according to claim 9, further comprising a step of collecting, into the sample bag, a component exiting from the separation column of the gas chromatograph at a predetermined timing among components exiting from the separation column when a first analysis-target gas is passed through the separation column, and a component exiting from the separation column within a time range exclusive of the predetermined timing among components exiting from the separation column when a second analysis-target gas which is different from the first analysis-target gas is passed through the separation column.

12. The odor evaluation method according to claim 9, further comprising a step of collecting, into the sample bag in which a predetermined gas is contained beforehand, a component exiting from the separation column of the gas chromatograph within a time range exclusive of a predetermined timing among components exiting from the separation column when an analysis-target gas is passed through the separation column.

13. The odor evaluation method according to claim 9, further comprising a step of measuring an odor of the gas in the sample bag by using an odor measurement device including m odor sensors which differ from each other in response characteristics, where m is an integer equal to or greater than two.

14. The odor evaluation method according to claim 9, further comprising a step of evaluating an odor of the gas in the sample bag by a sensory test using an olfactory sense.

15. A device for preparing a gas for odor evaluation, comprising:
    a gas chromatograph including a separation column configured to temporally separate a plurality of components contained in an odoriferous analysis-target gas;
    a first passage into which the plurality of components exiting from the separation column are introduced;
    a timing detector configured to detect, for each of the plurality of components, a timing at which the component exits from the separation column;
    a gas collector including an attachment port to which a sample bag is to be attached and a passage switcher configured to switch a condition of connecting the first passage and the attachment port, and configured to collect, into the sample bag, a gas containing all or some of the components exiting from the separation column when the analysis-target gas is passed through the separation column;
    a timing setter configured to set of a timing at which a component contained in the gas to be collected into the sample bag exits from the separation column based on a detection result of the timing detector; and
    a second passage connected to the first passage at a position between the separation column and the passage switcher;
    a gas introducer connected to the second passage and configured to introduce a dilution gas into the second passage.

* * * * *